(12) United States Patent
Boronse (10) Patent No.: US 10,948,587 B1
(45) Date of Patent: Mar. 16, 2021

(54) DEVICE FOR DETECTING EXPLOSIVE MATERIALS, OR WEAPONS OR FIREARMS, OR KNIVES OR SUBSTANCES

(71) Applicant: Adrien W. Boronse, Raleigh, NC (US)

(72) Inventor: Adrien W. Boronse, Raleigh, NC (US)

( * ) Notice: Subject to any disclaimer, the term of this patent is extended or adjusted under 35 U.S.C. 154(b) by 327 days.

(21) Appl. No.: 16/033,365

(22) Filed: Jul. 12, 2018

(51) Int. Cl.
| | |
|---|---|
| *G01S 13/88* | (2006.01) |
| *G01S 7/04* | (2006.01) |
| *G01S 13/42* | (2006.01) |
| *G01S 13/86* | (2006.01) |
| *H01J 49/42* | (2006.01) |
| *G01N 33/22* | (2006.01) |
| *G01N 27/622* | (2021.01) |
| *G01N 27/62* | (2006.01) |

(52) U.S. Cl.
CPC .......... *G01S 13/887* (2013.01); *G01N 27/622* (2013.01); *G01N 33/227* (2013.01); *G01S 7/046* (2013.01); *G01S 13/426* (2013.01); *G01S 13/867* (2013.01); *H01J 49/4225* (2013.01)

(58) Field of Classification Search
CPC .... G01S 13/887; G01S 13/426; G01S 13/867; G01S 7/046; H01J 49/4225; G01N 27/622; G01N 33/227
USPC .......................................................... 342/22
See application file for complete search history.

(56) References Cited

U.S. PATENT DOCUMENTS

| | | | | |
|---|---|---|---|---|
| 5,227,800 A | * | 7/1993 | Huguenin | G01S 7/024 250/332 |
| 6,359,582 B1 | * | 3/2002 | MacAleese | G01S 7/417 342/192 |
| 6,831,590 B1 | | 12/2004 | Steinway | |
| 2003/0085348 A1 | * | 5/2003 | Megerle | G01N 1/2202 250/287 |
| 2004/0053421 A1 | * | 3/2004 | Nguyen | G01N 21/76 436/172 |
| 2004/0114130 A1 | * | 6/2004 | Nguyen | G01N 1/24 356/36 |
| 2004/0169845 A1 | * | 9/2004 | Nguyen | G01N 1/24 356/36 |
| 2005/0122118 A1 | * | 6/2005 | Zank | G01D 9/005 324/457 |
| 2006/0050929 A1 | * | 3/2006 | Rast | G01S 3/784 382/103 |
| 2006/0081073 A1 | * | 4/2006 | Vandrish | G01N 1/2202 73/864.33 |

(Continued)

FOREIGN PATENT DOCUMENTS

| | | | | |
|---|---|---|---|---|
| WO | WO-2007089332 A2 | * | 8/2007 | .......... G01N 21/631 |
| WO | WO-2017031426 A1 | * | 2/2017 | ............... F41A 9/65 |

*Primary Examiner* — Timothy A Brainard
*Assistant Examiner* — Nuzhat Pervin
(74) *Attorney, Agent, or Firm* — Sanchelima & Associates, P.A.; Christian Sanchelima; Alexander J. Rodriguez (57) ABSTRACT

A device for detecting traces of explosive materials, weapons, firearms, knives or drugs is disclosed. The device is used a stand-alone device, or coupled to an explosive detector using mass spectrometry or ion mobility spectrometry technologies. The device comprises a plurality of sensors, a controller and a memory coupled to the processor. The sensors include radar, a position sensor, a camera and so on. The device scans a plurality of subjects in a field of regard. Based on the signals obtained from the sensors, the device determines presence of the explosive materials, weapons, firearms, knives or drugs and alerts a user of the device.

8 Claims, 6 Drawing Sheets

(56) References Cited

U.S. PATENT DOCUMENTS

| | | | |
|---|---|---|---|
| 2006/0087439 A1* | 4/2006 | Tolliver | G07C 9/37 340/573.1 |
| 2007/0221863 A1* | 9/2007 | Zipf | G01N 21/645 250/461.1 |
| 2008/0129581 A1* | 6/2008 | Douglass | G01S 13/34 342/52 |
| 2008/0191137 A1* | 8/2008 | Poteet | G01J 3/0278 250/338.1 |
| 2009/0032701 A1 | 2/2009 | Rodier | |
| 2009/0095901 A1* | 4/2009 | Robinson | H01J 49/145 250/283 |
| 2011/0174970 A1* | 7/2011 | Chalker | H01J 49/422 250/288 |
| 2012/0135537 A1* | 5/2012 | Horton | G01N 1/02 436/172 |
| 2014/0028457 A1* | 1/2014 | Reinpoldt | G06K 9/00771 340/552 |
| 2014/0062754 A1* | 3/2014 | Mohamadi | F41H 11/13 342/22 |
| 2014/0260542 A1* | 9/2014 | Nagano | G01N 1/2211 73/28.04 |
| 2016/0086466 A1* | 3/2016 | Foster | G08B 13/2494 348/143 |
| 2016/0097756 A1* | 4/2016 | Borkholder | G09B 19/00 73/35.15 |
| 2017/0051993 A1* | 2/2017 | Imbriano | F41A 19/01 |
| 2017/0160041 A1* | 6/2017 | Stewart | H04N 7/188 |
| 2018/0249133 A1* | 8/2018 | Thiel | H04N 5/2253 |
| 2020/0109909 A1* | 4/2020 | Stewart | F41A 35/00 |

* cited by examiner

DEVICE FOR DETECTING EXPLOSIVE MATERIALS, OR WEAPONS OR FIREARMS, OR KNIVES OR SUBSTANCES

BACKGROUND OF THE INVENTION

1. Field of the Invention

The present disclosure generally relates to detecting explosive materials, weapons, firearms, knives, and substances. More specifically, the present disclosure relates to a device for detecting explosive materials, weapons, firearms, knives, and drugs using radar, Ion Mobility Spectrometry (IMS), a Mass Spectrometry, and Explosive Trace Detector (ETD) technologies.

2. Description of the Related Art

It is known that explosive based weapons are used to carryout explosions in crowded areas. The explosive based weapons may include but not limited to RDX, PETN, TNT and so on. Reasons for increase in use of such explosive based weapons may include availability and easy to deploy such explosive based weapons. With increase in technology, novel methods have been invented to provide variety of compositions to make explosives, weapon delivery systems that are very difficult to trace or detect. Additionally, use of weapons such as firearms or guns, knives to create havoc in public places has increased.

Further, individuals are consuming controlled substances at large, which deteriorates health of the individuals. The controlled substances may include, but not limited to, marijuana, cocaine, heroin, PCP, methamphetamine and so on.

Typically, the explosives are detected by collecting vapor or particulate samples. The samples are analyzed with a sensitive sensor system using different techniques. Examples of the techniques include but not limited to an Ion Mobility Spectrometry (IMS), a Mass Spectrometry (MS), and a Gas Chromatography (GC).

Examples of the devices implementing the above techniques are deployed at airports, border security, government buildings and so on. Examples of the devices used to detect explosives, drugs and other objects are disclosed at least in a U.S.Pat. No. 6,831,590 and in a United States patent application 20090032701. In U.S. Pat. No. 6,831,590, a concealed object detection system for detecting objects concealed on a person is disclosed. The concealed object detection system includes radar transponders that are each configured and positioned to direct a radar signal at a person and to detect a portion of the radar signal reflected by the person. In US20090032701, a system for detecting analytes in a gas phase sample is disclosed. The system comprises an ion mobility spectrometer provided for detecting analytes having an excess amount of dopant in its separation region.

Although the devices are effective in detecting the explosives, weapons, firearms, knives and drugs, they are very bulky, expensive, and require time-consuming procedures. Further, the devices used to detect explosives, weapons, firearms, knives and drugs cannot be used at homes and cannot be mass-produced due to its overall cost and frequency of utilizing the devices to detect explosives, firearms, knives or drugs.

Other documents describing the closest subject matter provide for a number of more or less complicated features that fail to solve the problem in an efficient and economical way. None of these patents suggest the novel features of the present invention. Specifically, none of the disclosures in the art disclose a device comprising miniature sensors that are capable of detecting explosives, firearms, knives or drugs on their own or when connected with other devices that are capable of detecting explosives, firearms, knives or other controlled substances.

Therefore, there is a need in the art for a device that is portable, the device comprising sensors to detect explosives, weapons, firearms, knives, drugs and other controlled substances.

SUMMARY OF THE INVENTION

It is one of the main objects of the present invention to provide a device comprising a plurality of miniature sensors that are capable of detecting explosives, weapons, firearms, knives or drugs and avoids the drawbacks of the prior art.

It is one object of the present invention to provide a device capable of detecting traces of explosive materials, weapons, and drugs using radar technologies.

It is one object of the present invention to provide a device coupled to an explosive detector for detecting traces of explosive materials such as RDX, PETN, TNT and so on using an ion mobility spectrometry technology.

It is one object of the present invention to provide a device coupled an explosive trace detection system for detecting presence of explosives, weapons, firearms, or knives using an explosive trace detector technology.

It is one object of the present invention to provide a device for detecting traces of explosive materials, weapons, firearms, knives or drugs. The device comprises a plurality of sensors, a controller and a memory coupled to the processor. The sensors include radar, a position sensor, a camera and so on. The device scans a plurality of subjects in a field of regard. Based on the signals obtained from the sensors, the device determines presence of explosive materials and alerts a user of the device.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

The following detailed description is intended to provide example implementations to one of ordinary skill in the art, and is not intended to limit the invention to the explicit disclosure, as one or ordinary skill in the art will understand that variations can be substituted that are within the scope of the invention as described.

The present disclosure discloses a device for detecting traces of explosive materials, weapons, firearms, knives or drugs. In one example, the device may be used a stand-alone device. In another example, the device may be coupled to an explosive detector using mass spectrometry or ion mobility spectrometry technologies. The device comprises a plurality of sensors, a controller and a memory coupled to the processor. The sensors include radar, a position sensor, a camera and so on. The device scans a plurality of subjects in a field of regard. Based on the signals obtained from the sensors, the device determines presence of explosive materials, weapons, firearms, knives or drugs and alerts a user of the device.

When coupled to the explosive detector, mass spectrometry or ion mobility spectrometry technologies techniques are used to detect presence of explosives, weapons, firearms, knives or drugs. After detecting, the device displays results and alerts the user of the device.

Various features and embodiments of a device for detecting traces of explosive materials, weapons, firearms, knives or drugs are explained in conjunction with the description of FIGS. 1-6.

Figure 1:
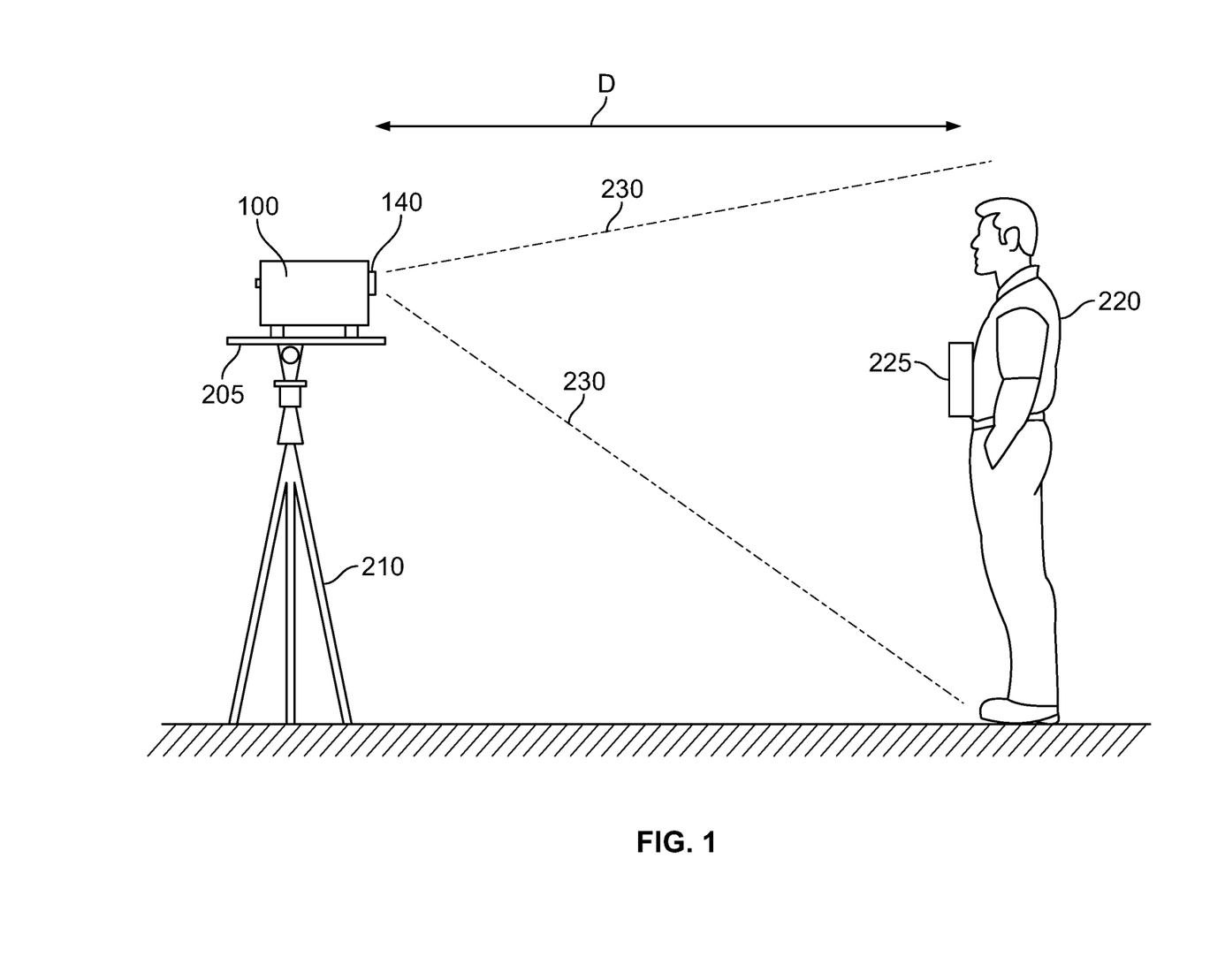
FIG. 1 illustrates a schematic diagram of a device 100 for detecting traces of explosive materials, weapons, firearms, and knives on a subject 220, in accordance with one embodiment of the present disclosure.
Figure 2:
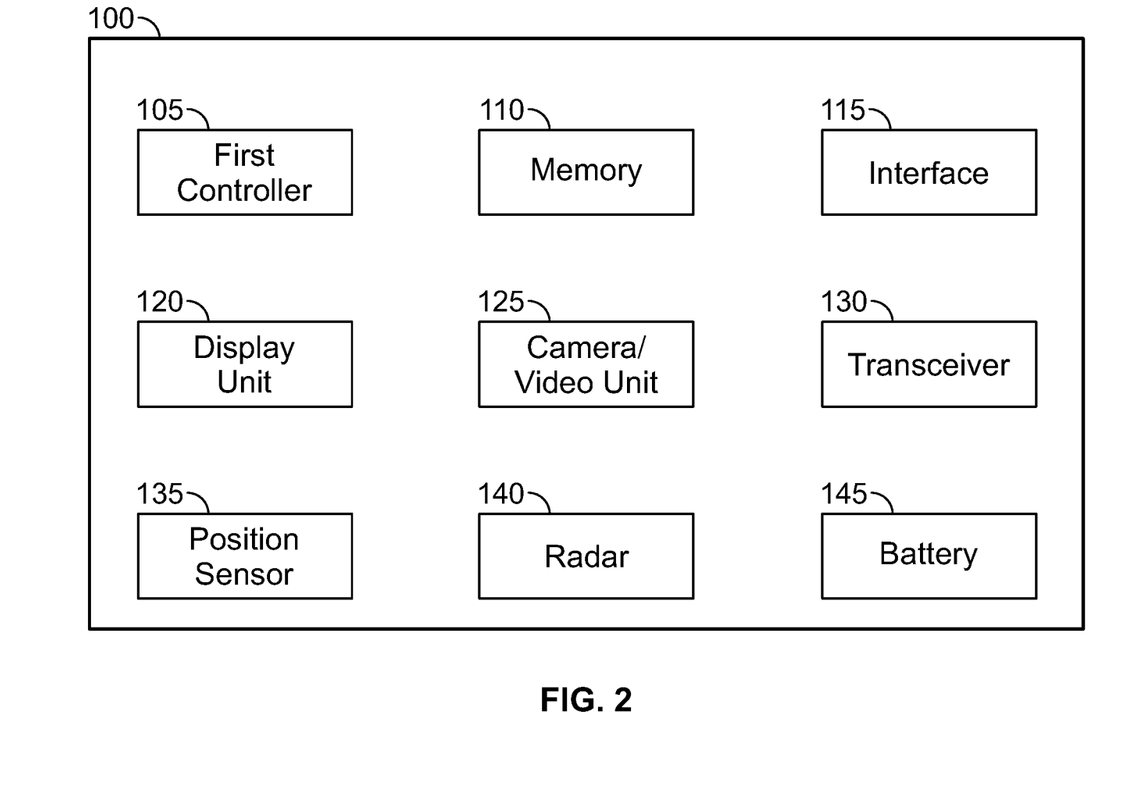
FIG. 2 illustrates the device 100 for detecting traces of explosive materials, in accordance with one embodiment of the present disclosure.

Referring to FIG. 1, a device 100 for detecting explosives, weapons, firearms, knives or drugs/controlled substances is shown, in accordance with one embodiment of the present disclosure. The device 100 may include, but not limited to, an electronic device such as a mobile phone, a laptop, a camera, a desktop, and so on. Referring to FIG. 2, the device 100 comprises a controller 105, a memory 110, an interface 115, a display unit 120, a camera or video unit 125, a transceiver 130, a position sensor 135, radar 140 and a battery 145.

The controller 105 may be implemented as one or more microprocessors, microcomputers, digital signal processors, central processing units, state machines, logic circuitries, and/or any devices that manipulate signals based on operational instructions. Among other capabilities, the controller 105 is configured to fetch and execute computer-readable instructions or program instructions stored in the memory 105.

The memory 110 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, and so on.

The interface 115 may include a variety of software and hardware interfaces, for example, a web interface, a graphical user interface, and the like. The interface 115 may allow the control unit 105 to interact with the user or customer directly or through other devices (not shown). In one example, the interface 115 may include a touch screen interface.

The display unit 120 may include a Light Emitting Diode (LED) or Liquid Crystal Display (LCD) screen configured to display text or video.

The camera or video unit 125 indicates an imaging unit used to capture still images or a video.

The transceiver 130 is used to transmit and receive signal/data from the controller 105 to external devices such as servers, scanners, explosive detectors, or other devices.

The position sensor 135 may indicate a location sensor such a Global Positioning System (GPS) sensor.

The radar 140 includes a radar sensor or a radar antenna. The radar 140 is used to launch electromagnetic Radio Frequency (RF) energy or radar pulse frequency.

The battery 145 may include but not limited to a rechargeable battery made up of Lithium Ion to power the device 100.

Referring to FIG. 1, the device 100 may be carried by a user or may be placed on a placed on a platform 205. In one example, the platform may be mounted on a stand 210 as shown in FIG. 1. The device 100 is positioned such that the camera 125 and the radar 140 face a subject 220. The subject 220 may indicate a person or a group of people whom a user wishes to screen for explosive materials or drugs. In one example, the subject 220 may include an object such as baggage of the person, a container being transported from one place to another. The subject 220 may be asked to stand at a distance D from the device 100. In one example, the distance D may range from 2 meters to 10 meters. Consider that the subject 220 has a threat device 225 e.g., an explosive device/bomb, a gun/firearm, a knife and so on. When the subject 220 is standing at the distance D, the camera 125 and radar 140 may have a field of view or field of regard 230, as shown in FIG. 1. As specified above, the field of regard 230 may have a group of people and the device 100 may be used to scan the group of people in the field of view or field of regard 230.

In order to detect the threat device 225 carried by the subject 220, at first, the subject 220 shall be within the field of view 230 of the device 100. Subsequently, the user of the device 100 may navigate options provided at the interface 115 on the display unit 120. The user may select an option to scan the subject 220. Upon selecting, the radar 140 may beam or launch electromagnetic Radio Frequency (RF) energy or radar pulse frequency in the filed of regard 230. As known, the electromagnetic Radio Frequency (RF) energy or radar pulse frequency allows to detect radar signatures of man-made objects such as the explosives.

The radar beam launched by the radar 140 intersects the subject 220 and the threat device 225 within the distance D. Further, the energy scattered off the subject 220 and the threat device 225 is collected by the transceiver 130. Subsequently, the transceiver 130 sends signals to the controller 105. The signals received at the controller 105 are provided in a digital format. After receiving the signals from the transceiver 130, the controller 105 executes a plurality of signal processing algorithms stored in the memory 110. The controller 105 executes the plurality of signal processing algorithms to classify the signals received from the subject 220 as threat or non-threat.

If the controller 105 classifies that the signals received from the subject 220 are non-threat, then the controller 105 may instruct the display unit 120 to display a signal or sign e.g., green color light indicating that the subject 220 is not a threat. If the controller 105 classifies that the signals received from the subject 220 are threat, then the controller 105 may instruct the display unit 120 to display a signal or sign e.g., red color light indicating that the subject 220 is a threat. Further, the controller 105 may instruct the device 100 to raise an audible alarm such that the user of the device 100 is made aware of the subject 220 carrying the threat device 225.

After detecting that the subject 220 is carrying the threat device 225, the controller 105 may instruct the camera 125 to capture an image of the subject 220. In addition, the controller 105 may instruct the camera 125 to capture an image of the threat device 225. Subsequently, the image of the subject 220 and the threat device 225 may be displayed on the display unit 120.

In one example, the controller 105 may instruct the position sensor 135 to determine the position of the subject 220 if there is more number of people in the field of view or field of regard 230. Determining the position or location of the subject 220 may help in capturing the subject 220.

Based on the above, the device 100 is used to analyze the subjects 220 within the field of regard and to detect polarization signatures that are characteristic of a subject carrying the threat device 225. Further, the camera or video unit 125 is used to identify or track the subjects 220.

Figure 3:
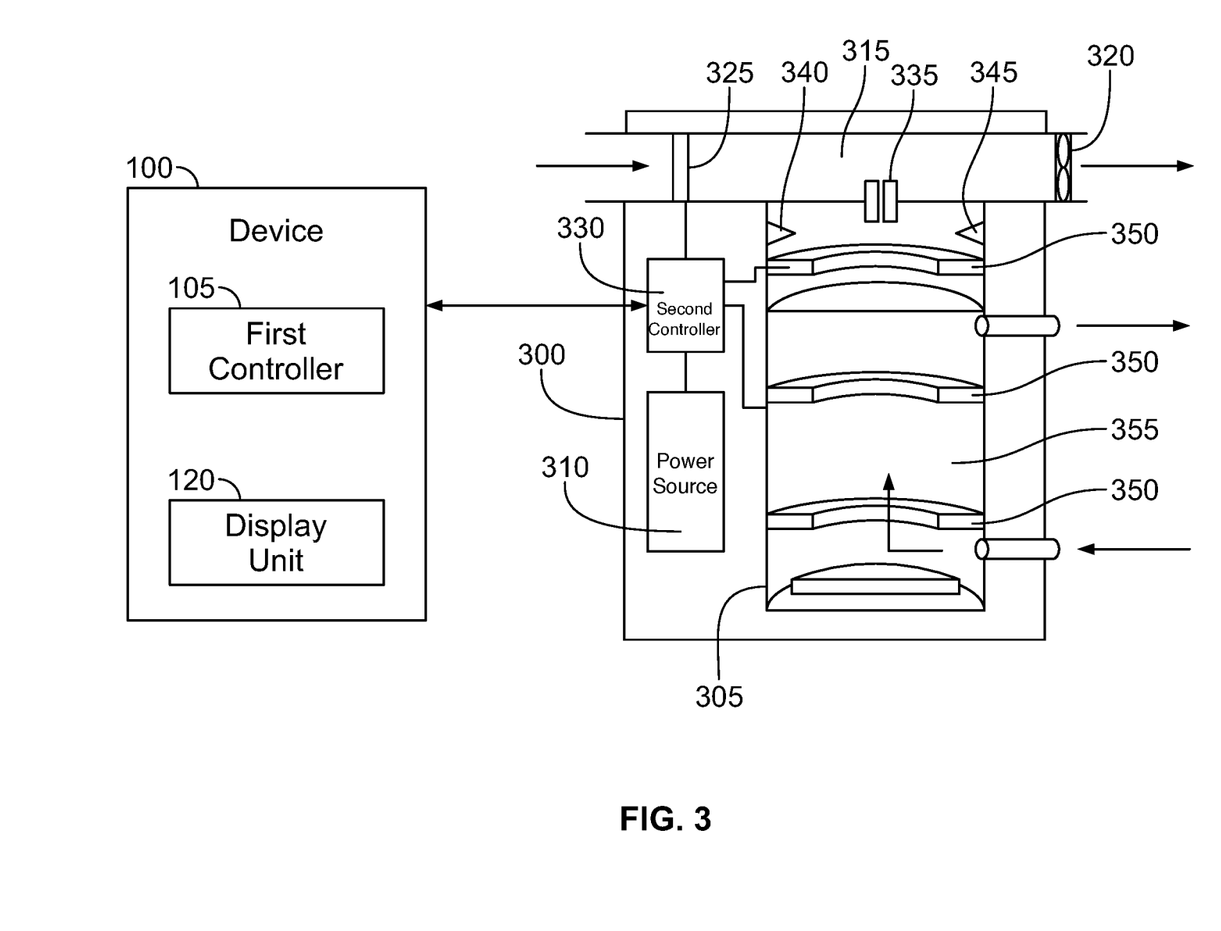
FIG. 3 illustrates a schematic diagram of the device 100 coupled to an explosive detector 300 for detecting traces of explosive materials or firearms in accordance with one embodiment of the present disclosure.

In another implementation, the device 100 may be coupled to an explosive detector to detect explosives, weapons, firearms, and knives. The explosives may include RDX, Pentaerythritol Tetranitrate (PETN), Trinitrotoluene (TNT), Nitroglycerin, Aziroazide azide and so on. The weapons may include but not limited to handgun, a hand grenade, or a long knife. Further, examples of the firearms may include rifles, shotguns, carbines, machine guns, submachine guns, automatic rifles, assault rifles, personal defense weapon, and fire lances. Referring to FIG. 3, the device 100 coupled to an explosive detector 300 is shown, in accordance with one embodiment of the present disclosure. The explosive detector 300 comprises an Ion Mobility Spectrometer (IMS) 305, a power source 310 for providing power to the explosive detector 300. Further, the explosive detector 300 comprises an inlet 315, and an air mover 320 for drawing a flow of air through the inlet 315. The inlet 315 comprises a passage (not shown) through which a flow of air to be sampled by the IMS 305 can flow.

Further, the explosive detector 300 comprises a heater 325 configured to heat the air to be tested. The explosive detector 300 comprises a second controller 330 configured to control the air mover 320, the IMS 315, and the heater 325. As can be seen from FIG. 3, the device 100 is communicatively coupled to the explosive detector 300. Specifically, the second controller 330 is communicatively coupled to the device 100.

The IMS 305 is coupled to the inlet 315 by a sampling port 335. The explosive detector 300 comprises a reaction region 340 in which a sample can be ionized. The sampling port 335 can be operated to obtain a sample from the inlet 315 into the IMS 305. The sampling port 335 can be operated to sample air from the inlet 315 into the reaction region 340 of the IMS 305. The reaction region 340 comprises an ionizer 345 for ionizing the sample. Further, the explosive detector 300 comprises a drift chamber 355 comprising drift electrodes 350 for applying an electric field along the drift chamber 355 to accelerate ions bottom of the IMS 305 against the flow of the drift gas.

In order to activate the IMS 305 to detect the explosives, the weapons, the firearms and the knives, the user of the device 100 may select an option by navigating on the interface 115 provided on the display unit 120. Subsequently, the controller 105 instructs the second controller 330 to activate the IMS 305. The second controller 330 activates the IMS 305 and operates the air mover 320 so that a flow of air is drawn through the inlet 315. Further, the second controller 330 increases the heat output from the heater 325 for a selected time period. The time period may be selected based on the type of explosive or drug that the user wishes to detect.

After completion of the time period, the second controller 330 controls the sampling port 335 to obtain the sample from the heated flow of air in the inlet 315. Further, the second controller 330 controls the IMS 305 to perform ion mobility spectrometry on the heated sample in the reaction region 340. Subsequently, the second controller 330 operates the electrodes 350 to apply an electric charge to aerosol particles in the sample. Upon applying the electric charge, the electrodes 350 draw the aerosol particles onto the electrodes 350. After drawing the aerosol particles, the second controller 330 sends signals indicating presence of the explosives/firearms/knives to the controller 105 of the device 100.

Subsequently, the controller 105 may instruct the display unit 120 to display a signal or sign e.g., red color light indicating that the sample comprises explosive material or weapon or firearm or knife. Further, the controller 105 may instruct the device 100 to raise an audible alarm such that the user of the device 100 is made aware of the explosive material or firearm or knife being carried by the subject.

Figure 4:
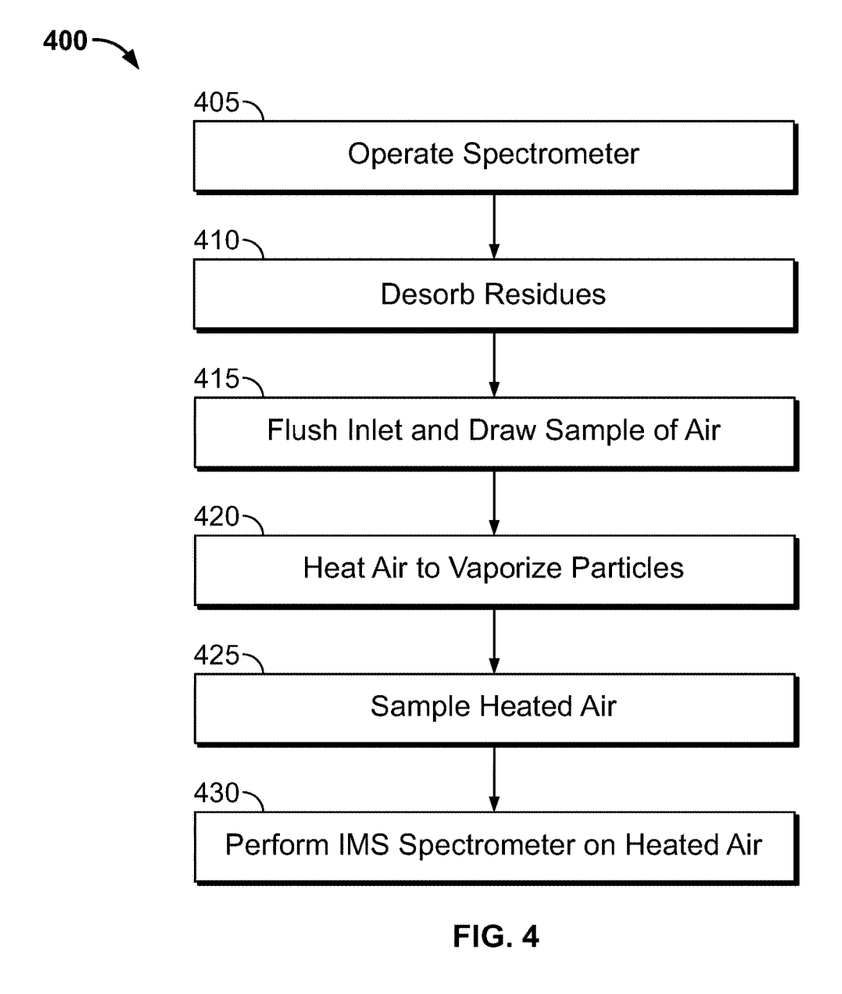
FIG. 4 illustrates a method 400 for detecting traces of explosive materials, weapons, firearms or knives using the explosive detector 300, in accordance with one embodiment of the present disclosure.

Referring to FIG. 4, a method 400 of detecting explosives or weapons or firearms or knives with the help of the explosive detector 300 is shown, in accordance with an embodiment of the present disclosure. The method 400 may be described in a sequence of steps to be performed for detecting explosives. However, the order in which the method 400 is described and is not intended to be construed as a limitation, and any number of the described method blocks can be combined in any order to implement the method 400 or alternate methods. Additionally, individual blocks may be deleted from the method 400 without departing from scope of the disclosure described herein. For ease of explanation, in the embodiments described below, the method 400 may be implemented in the above-described device 100 and the explosive detector 300.

At step 405, the device 100 is used to operate the spectrometer (IMS) 305. The IMS 305 is activated and the air mover 320 is operated to draw a flow of air through the inlet 315.

At step 410, the inlet 315 is heated so that residues can be desorbed from the IMS 305.

At step 415, the residue is flushed out of the inlet 315 with the help of the air mover 320.

At step 420, the air is heated to vapourise an aerosol carried by the air.

At step 425, a sample is obtained from the air heated.

Figure 5:
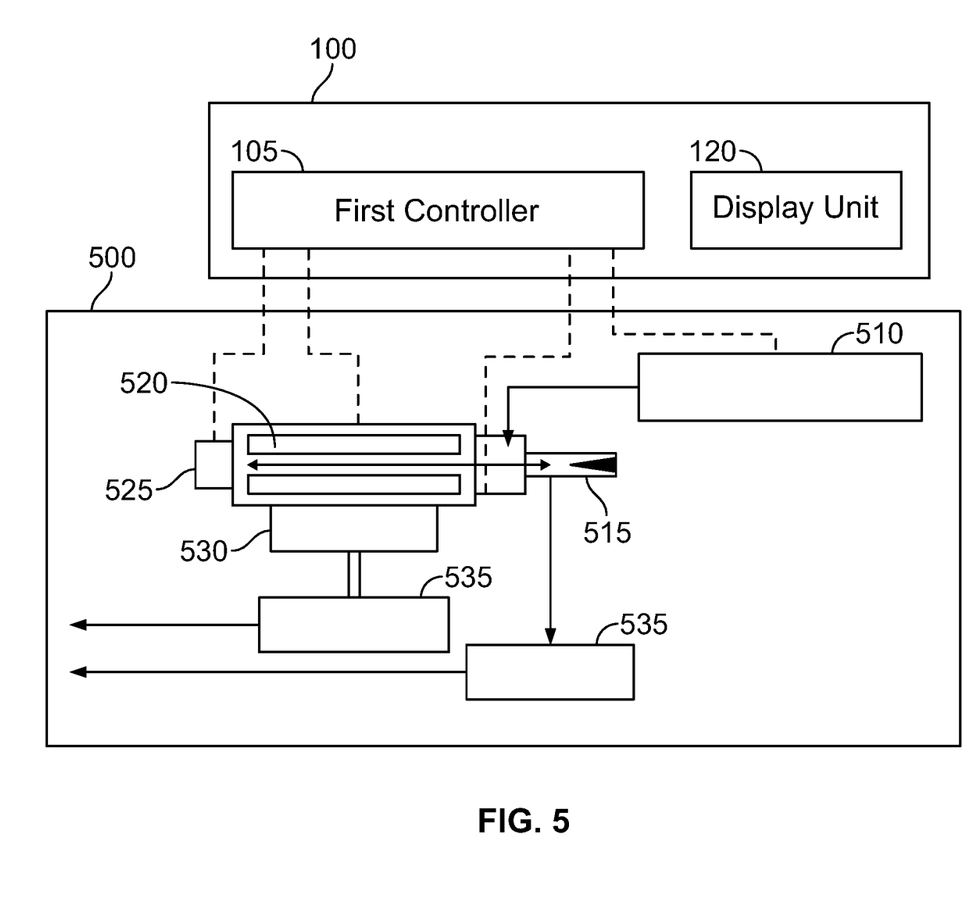
FIG. 5 illustrates a schematic diagram of the device 100 coupled to an explosive trace detection system 500 for detecting traces of explosive materials, weapons, firearms, knives or drugs, in accordance with one embodiment of the present disclosure.

At step 430, the heated air is analysed by the IMS 305. Specifically, the ion mobility spectrometry is performed on the heated air to draw the aerosol particles onto the electrodes 350. Subsequently, the second controller 330 sends signals to the device 100 indicating that the aerosol is found in the sample.

In yet another implementation, the device 100 may be coupled to an explosive trace detection system to detect presence of explosives, weapons and drugs. Referring to FIG. 5, the device 100 coupled to an explosive trace detection system 500 is shown, in accordance with one embodiment of the present disclosure. The explosive trace detection system 500 comprises a sampling unit 510, an Ion Source 515, a Quadrupole Mass Spectrometry (QMS) 520, a conversion-scanning electron microscope (C-SEM) 525, a turbo molecular pump 530 and pumps 535.

At first, the device 100 is coupled to the explosive trace detection system 500 through a wired connection or through a wireless mechanism. In one example, the explosive trace detection system 500 is provided with a third controller (not shown) and a second transceiver (not shown) to communicate with the device 100.

In order to detect explosives or weapons or firearms or knifes, at first, the sample is collected. Specifically, the sample is collected on a sheet (not shown). After collecting the sample, the sheet is inserted into the sampling unit 510. Subsequently, the sample comprising constituents is ionized with the help of ion source 515. In order to ionize the sample, the sample is heated to an appropriate temperature and the constituents are vaporized. After vaporizing, sample gas is made to travel through the ion source 515 and ionized. After ionization, molecular mass of the sample is measured using QMS 520.

After measuring the molecular masses of the sample, the QMS 520 sends the results to the controller 105. Based on the molecular masses of the sample, the controller 105 identifies the material of the sample. The material may be identified as one of explosive material, the firearm, a compound of a substance i.e., drug. After determining, the controller 105 instructs the display unit 120 to display the results of the molecular masses of the sample, type of explosive material, or firearm or drug and so on. Further, the controller 105 may instruct the display unit 120 to display a signal or sign e.g., red color light indicating that the sample comprises explosive material or firearm or drug. Further, the controller 105 may instruct the device 100 to raise an audible alarm such that the user of the device 100 is made aware of the explosive material or firearm or drug being present in the sample.

Figure 6:
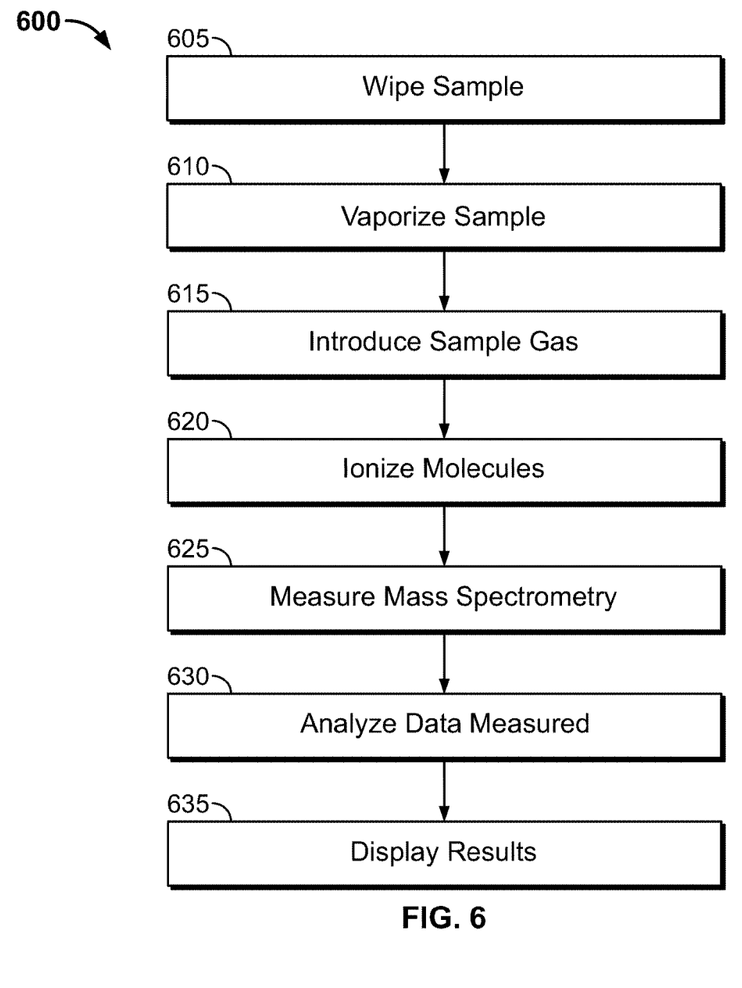
FIG. 6 illustrates a method 600 for detecting traces of explosive materials, weapons, firearms, knives or drugs using the explosive trace detection system 500, in accordance with one embodiment of the present disclosure.

Referring to FIG. 6, a method 600 of detecting explosives with the help of the explosive trace detection system 500 is shown, in accordance with an embodiment of the present disclosure. The method 600 may be described in a sequence of steps to be performed for detecting explosives. However, the order in which the method 600 is described and is not intended to be construed as a limitation, and any number of the described method blocks can be combined in any order to implement the method 600 or alternate methods. Additionally, individual blocks may be deleted from the method 600 without departing from scope of the disclosure described herein. For ease of explanation, in the embodiments described below, the method 600 may be implemented in the above-described device 100 and the explosive trace detection system 500.

At step 605, the sample is collected or wiped on the sheet.

At step 610, the sample is heated to vaporize constituents of the sample.

At step 615, sample gas is introduced into the ion source 515.

At step 620, the molecules of the sample are ionized.

At step 625, the QMS 520 measures the molecular masses of the sample using mass spectrometry.

At step 630, the controller 105 analyzes data corresponding to the molecular masses to identify the type of explosive.

At step 635, the controller 105 instructs the display unit 120 to display the results. Further, the controller 105 instructs the device 100 to raise an audible alarm.

Based on the above, it is evident the device 100 can be used to detect presence of explosive material, weapons, drugs, guns, or knives. It should be understood that the device 100 can be used as a stand-alone device to detect presence of explosive material or may be used with an explosive detector or explosive trace detection system to detect presence of explosive material.

The device may employ radar technology, ion mobility spectrometry or explosive trace detector to detect presence of explosive material. As such, the device can be used at home or any other place to detect traces of explosive materials, weapons or drugs.

It should be understood the device displays the image of the threat device, and the image of the subject carrying the threat device on the display unit. Further, the device is configured to display the distance from the subject carrying the explosive materials, weapons, firearms, knives or drugs. In one exemplary embodiment, the device may be configured to alert emergency personnel such police upon detecting the explosive materials, weapons, firearms, knives or drugs.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A device for detecting traces of explosive materials, weapons, firearms, knives or drugs, the device comprising:
   a plurality of sensors;
   a controller;
   a memory coupled to the controller, wherein the controller executes program instructions stored in the memory, to:
      scan a plurality of subjects in a field of regard;
      determine presence of explosive materials based on signals obtained; and
      identify a subject carrying the explosive materials, weapons, firearms, knives or drugs and alert a user of the device;
   wherein said device is coupled to an explosive detector which includes an Ion Mobility Spectrometer (IMS), a power source, an inlet, and an air mover for drawing a flow of air through the inlet, wherein said explosive detector further includes a heater which heats said flow or air to be tested, wherein said explosive detector further includes a second controller which is in communication with said air mover, said IMS, and said heater, wherein said IMS is coupled to said inlet by a sampling port, wherein said sampling port extends within said inlet and within said IMS; and
   wherein said device is coupled to an explosive trace detection system which includes a sampling unit, an ion source, a quadrupole mass spectrometry (QMS), a conversion-scanning electron microscope (C-SEM), a turbo molecular pump, and pumps, wherein said explosive trace detection system receives a sample to be tested and then measures and identifies a molecular mass of said sample.

2. The device of claim 1, wherein the plurality of sensors comprises one of a position sensor, a radar, and a camera.

3. The device of claim 2, wherein the position sensor determines a distance between the device and the subject.

4. The device of claim 3, wherein the camera captures the image of the subject and the explosive materials or the weapons or the firearms or the knives or the drugs upon determining the presence of the explosive materials or the weapons or the firearms or the knives or the drugs on the subject.

5. The device of claim 4, further comprises a display unit to display the image of the subject, wherein the display unit displays the position of the subject and the distance between the device and the subject.

6. The device of claim 1, wherein the alert is a visual alert or audio alert.

7. The device of claim 1, wherein the controller processes the signals obtained from the sensors to classify the explosive materials detected into one of the explosive materials, the weapons, the firearms, the knives, and the drugs.

8. A portable handheld security detection device for detecting traces of explosive materials, weapons, firearms, knives or drugs, consisting of:
- a) a controller unit being selected from a group consisting essentially of a microprocessor, a microcomputer, a digital signal processor, a central processing unit, a state machine, or a logic circuit, wherein said controller executes a computer readable program instruction stored in a memory;
- b) an interface being a graphical user interface, wherein said interface communicates with said controller unit;
- c) a display unit being a light emitting diode screen configured to display text or video;
- d) a camera or video unit configured to capture images or video;
- e) a transceiver which transmits and receives signal and data from the controller unit to external devices;
- f) a position sensor being a global positioning sensor;
- g) a radar being a radar sensor or a radar antenna which launches electromagnetic radio frequency energy;
- h) a rechargeable battery made of lithium ion configured to power said device;
- i) a platform having a stand, wherein said device is mounted on said stand;
- j) wherein said radar launches the electromagnetic radio frequency energy in a field of regard to scan a subject and a threat device, wherein energy signals being scattered of said subject and said threat device are collected by said transceiver, wherein in said transceiver transmits said energy signals collected to the controller unit, wherein said controller unit executes a plurality of signal processing algorithms upon receiving the energy signals from the transceiver to then classify the data received as a threat or a non-threat, wherein said display unit then displays a sign indicating if said subject or threat device is a threat or non-threat;
- k) wherein said device is coupled to an explosive detector which includes an Ion Mobility Spectrometer (IMS), a power source, an inlet, and an air mover for drawing a flow of air through the inlet, said explosive detector further including a heater configured to heat air and a second controller which communicates with said air mover, said IMS, and said heater, wherein said IMS is coupled to said inlet by a sampling port; and
- l) wherein said device is coupled to an explosive trace detection system which includes a sampling unit, an Ion Source, A Quadrupole Mass Spectrometry (QMS), a conversion-scanning electron microscope (C-SEM), a turbo molecular pump, and pumps, wherein said display unit displays data of molecular masses of a sample inserted into the explosive trace detection system.

\* \* \* \* \*